(12) United States Patent
Otsubo et al.

(10) Patent No.: US 7,220,251 B2
(45) Date of Patent: May 22, 2007

(54) PANTS-TYPE DISPOSABLE WEARING ARTICLE

(75) Inventors: Toshifumi Otsubo, Kagawa-ken (JP); Shunsuke Takino, Kagawa-ken (JP); Nariaki Shimoe, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 63 days.

(21) Appl. No.: 10/839,709

(22) Filed: May 6, 2004

(65) Prior Publication Data

US 2005/0004548 A1 Jan. 6, 2005

Related U.S. Application Data

(63) Continuation of application No. PCT/JP03/00853, filed on Jan. 29, 2003.

(30) Foreign Application Priority Data

Jan. 31, 2002 (JP) ............................. 2002-024374

(51) Int. Cl.
*A61F 13/494* (2006.01)
*A61F 13/496* (2006.01)

(52) U.S. Cl. ................... 604/385.201; 604/385.27; 604/385.21; 604/396

(58) Field of Classification Search ........... 604/385.02, 604/385.25, 385.201, 385.24, 385.23, 385.27
See application file for complete search history.

(56) References Cited

U.S. PATENT DOCUMENTS

| 1,300,510 | A | * | 4/1919 | Steele | 604/398 |
|---|---|---|---|---|---|
| 3,196,874 | A | * | 7/1965 | Hrubecky | 604/366 |
| 3,710,797 | A | * | 1/1973 | Marsan | 604/385.201 |
| 3,744,494 | A | * | 7/1973 | Marsan | 604/378 |
| 3,776,233 | A | * | 12/1973 | Schaar | 604/385.23 |
| 3,794,033 | A | * | 2/1974 | Ryan | 604/365 |
| 3,807,402 | A | * | 4/1974 | Miller et al. | 604/378 |
| 3,924,626 | A | * | 12/1975 | Lee et al. | 604/366 |
| 3,924,627 | A | * | 12/1975 | Nystrand | 604/365 |
| 3,951,150 | A | * | 4/1976 | Schaar | 604/389 |
| 3,968,799 | A | * | 7/1976 | Schrading | 604/365 |
| 4,897,084 | A | * | 1/1990 | Ternstrom et al. | 604/385.27 |
| 4,917,696 | A | * | 4/1990 | De Jonckheere | 604/385.27 |
| 5,037,415 | A | * | 8/1991 | Leroy et al. | 604/385.25 |

(Continued)

FOREIGN PATENT DOCUMENTS

JP 50-21845 3/1975

(Continued)

*Primary Examiner*—Tatyana Zalukaeva
*Assistant Examiner*—Paula L. Craig
(74) *Attorney, Agent, or Firm*—Lowe Hauptman & Berner LLP

(57) ABSTRACT

A pull-on disposable article has a liquid-absorbent first panel interposed between a liquid-absorbent sheet and liquid-impervious sheets, a waist-hole and a pair of leg-holes. The leg-holes are surrounding by leg-surrounding flaps extending in a leg-surrounding direction outside transversely opposite side edges of the first panel. A transverse dimension between the transversely opposite side edges is minimized in the vicinity of bottoms of the respective leg-holes. The leg-surrounding flaps are formed with first folding lines extending in the leg-surrounding direction and second folding lines extending in a transverse direction. The leg-surrounding flaps are tucked along the first and second folding lines into the respective leg-holes.

5 Claims, 9 Drawing Sheets

U.S. PATENT DOCUMENTS

| | | | |
|---|---|---|---|
| 5,401,275 A * | 3/1995 | Flug et al. | 604/391 |
| 5,447,508 A * | 9/1995 | Numano et al. | 604/385.27 |
| 5,690,626 A * | 11/1997 | Suzuki et al. | 604/385.25 |
| 5,746,730 A * | 5/1998 | Suzuki et al. | 604/385.26 |
| 5,916,206 A * | 6/1999 | Otsubo et al. | 604/385.27 |
| 6,102,892 A * | 8/2000 | Putzer et al. | 604/385.01 |
| 6,165,160 A * | 12/2000 | Suzuki et al. | 604/385.201 |
| 6,174,303 B1 * | 1/2001 | Suprise et al. | 604/385.29 |
| 6,210,387 B1 * | 4/2001 | Rudberg et al. | 604/385.27 |
| 6,623,468 B2 * | 9/2003 | Shimoe | 604/385.27 |
| 6,635,041 B1 * | 10/2003 | Popp et al. | 604/385.25 |
| 6,652,504 B1 * | 11/2003 | Olson et al. | 604/385.25 |
| 6,666,851 B2 * | 12/2003 | Otsubo et al. | 604/385.201 |
| 6,702,799 B2 * | 3/2004 | Otsubo | 604/385.21 |
| 7,112,189 B2 * | 9/2006 | Otsubo et al. | 604/201 |
| 7,169,136 B2 * | 1/2007 | Otsubo et al. | 604/385.21 |
| 7,172,583 B2 * | 2/2007 | Otsubo et al. | 604/385.201 |
| 2004/0133178 A1 * | 7/2004 | Otsubo et al. | 604/385.01 |

FOREIGN PATENT DOCUMENTS

| | | |
|---|---|---|
| JP | 50-33044 | 3/1975 |
| JP | 11-104177 | 4/1999 |
| JP | 11-104180 | 4/1999 |
| JP | 11-155904 | 6/1999 |
| JP | 11-169403 | 6/1999 |
| JP | 2002-035033 | 2/2002 |
| JP | 2003-010244 | 1/2003 |
| WO | WO 02/096333 | * 12/2002 |

* cited by examiner

PANTS-TYPE DISPOSABLE WEARING ARTICLE

This application is a continuation of PCT Application No. PCT/JP03/00853 filed Jan. 29, 2003, which claims priority to Japanese Application No. 2002-024374 filed Jan. 31, 2002.

BACKGROUND OF THE INVENTION

This invention relates to a pants-type disposable wearing article for absorption and retainment of bodily discharges.

The pants-type disposable wearing article is well known, which comprises a liquid-pervious topsheet, a liquid-impervious backsheet and a liquid-absorbent panel interposed between these two sheets so as to define front and rear waist regions opposed to each other and a crotch region extending between these waist regions wherein the front and rear waist regions are connected to each other along transversely opposite side edge portions of these waist regions which are overlaid to form a waist-hole and a pair of leg-holes.

The leg-holes are surrounded by associated leg-surrounding flaps extending along outer edges of the associated side edge portions of the panel in a leg-surrounding direction. The leg-surrounding flaps have free side edges curving inwardly in a transverse direction of the article from tops toward bottoms of the respective leg-holes so that a transverse dimension between the free side edges is minimized in the vicinity of the bottoms of the respective leg-holes. In this article of well known art, a transverse dimension of the crotch region is smaller than a transverse dimension each of the front and rear waist regions has. In other words, with the front and rear waist regions disconnected from each other and then developed, the article has a hourglass-like planar shape. Such pants-type wearing article is disclosed, for example, in Japanese Patent Unexamined Publication Nos. 1999-104177A; 1999-104180A; 1999-155904A; and 1999-169403A.

When the above-cited wearing article of well known art is viewed from above the waist-hole being opened, it is found that the leg-holes are opened in the transverse direction of the article while the waist-hole is opened in the longitudinal direction of the article. With a consequence, the waist-hole is not in alignment with the leg-holes and the leg-surrounding flaps extending in the vicinity of the bottoms of the respective leg-holes lie ahead of the waist-hole. In the case of this article, there is an anxiety that the wearer's toes and/or heels might get stuck with the leg-surrounding flaps lying in the vicinity of the bottoms of the leg-holes as the wearer intends to guide his or her legs through the waist-hole then through the leg-holes. As a result, it is likely that the operation of wearing the article might be inconveniently retarded.

In this article, a transverse dimension of the crotch region in the vicinity of the bottoms of the respective leg-holes is larger than a transverse dimension of the wearer's crotch and the crotch region of the article can not be fitly put in the crotch of the wearer after the article has been put on the wearer's body. Consequently, the crotch region of the article becomes bulky and the wearer experiences an uncomfortable feeling. With the article, the leg-surrounding flaps are irregularly folded or the panel is formed with a plurality of irregular wrinkles as the crotch region of the article is squeezed in the crotch region of the wearer. These folds or wrinkles may sometimes deteriorate an absorbing capacity for bodily discharges in the crotch region and even allow the bodily discharge to leak from the crotch region.

The transverse dimension of the wearer's crotch is generally in a range of 3–8 cm. In many of the articles on the market, the minimum dimension of the panel in the crotch region is generally in a range of 10–20 cm and the minimum dimension between the transversely opposite free outer side edge portions of the leg-surrounding flaps in the crotch region is generally in a range of 15–30 cm. In the articles on the market, therefore, the transverse dimension of the crotch region in the vicinity of the bottoms of the respective leg-holes is larger than the transverse dimension of the wearer's crotch.

SUMMARY OF THE INVENTION

It is an object of this invention to provide a pants-type disposable wearing article having its crotch region adapted to be fitly put in the wearer's crotch so that the article can be put on the wearer's body without being retarded and the wearer can be free from experiencing an uncomfortable feeling.

According to this invention, there is provided a pants-type disposable wearing article comprising a liquid-absorbent sheet facing a wearer's body, a liquid-impervious sheet facing away from the wearer's body and a liquid-absorbent first panel between these sheets, the article further having a waist-hole and a pair of leg-holes surrounded by leg-surrounding flaps extending in a leg-surrounding direction outside transversely opposite side edges of the first panel wherein a transverse dimension between the transversely opposite side edges of the first panel is minimized in the vicinity of bottoms of the respective leg-holes.

This invention further comprises the leg-surrounding flaps formed with a first folding line extending in the leg-surrounding direction from the side edges of the first panel in the vicinity of the bottoms of the respective leg-holes toward free side edges of the respective leg-surrounding flaps lying in the vicinity of tops of the leg-holes and a second folding line extending outwardly in a transverse direction from the side edges of the first panel lying in the vicinity of the bottoms of the leg-holes toward the free side edges of the leg-surrounding flaps lying in the vicinity of the bottoms of the leg-holes. The leg-surrounding flaps lying in the vicinity of the bottoms of the leg-holes rise above the first panel and the free side edges of the leg-surrounding flaps get nearer to each other in the transverse direction as the leg-surrounding flaps are folded along the first and second folding lines and tucked inwardly in the transverse direction into the leg-holes.

This invention includes the following embodiments. The minimum spacing dimension between the free side edges of the leg-surrounding flaps lying in the vicinity of the bottoms of the leg-holes is substantially same as the minimum transverse dimension between the side edges of the first panel lying in the vicinity of the bottoms of the leg-holes.

The minimum transverse dimension between the opposite side edges of the first panel lying in the vicinity of the bottoms of the leg-holes is in a range of 2–9 cm.

Leg-surrounding elastic members extending in the leg-surrounding direction are attached in a stretched state to the leg-surrounding flaps.

The free side edges of the leg-surrounding flaps curve inwardly in the transverse direction of the article from the tops toward the bottoms of the leg-holes so that a transverse dimension between the free side edges of the leg-surrounding flaps is minimized in the vicinity of the bottoms of the leg-holes.

Liquid-absorbent second panels interposed between the liquid-pervious sheet and the liquid-impervious sheet are provided in regions defined between vicinities of the first folding lines and the free side edges of the leg-surrounding flaps and tucked with the leg-surrounding flaps inwardly in the transverse direction into the respective leg-holes.

The second panels have a relatively low stiffness or none of the second panels is present on the second folding lines as well as in the vicinity of these second folding lines.

DETAILED DESCRIPTION OF THE PREFERRED EMBODIMENTS

Details of the pants-type disposable wearing article according to this invention will be more fully understood from the description given hereunder in reference to the accompanying drawings.

Figure 1:
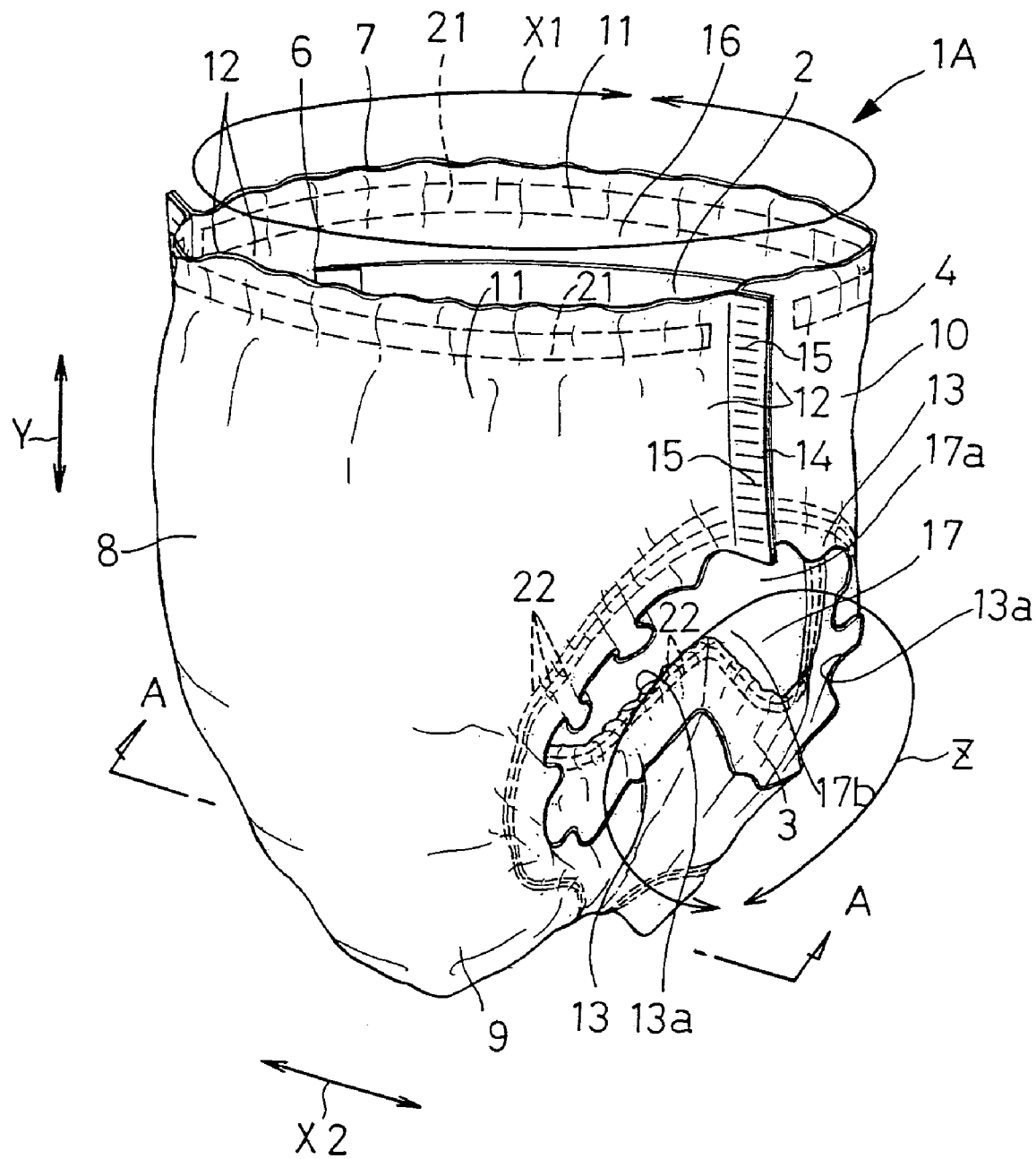
FIG. 1 is a perspective view showing an embodiment of disposable wearing article.
Figure 2:
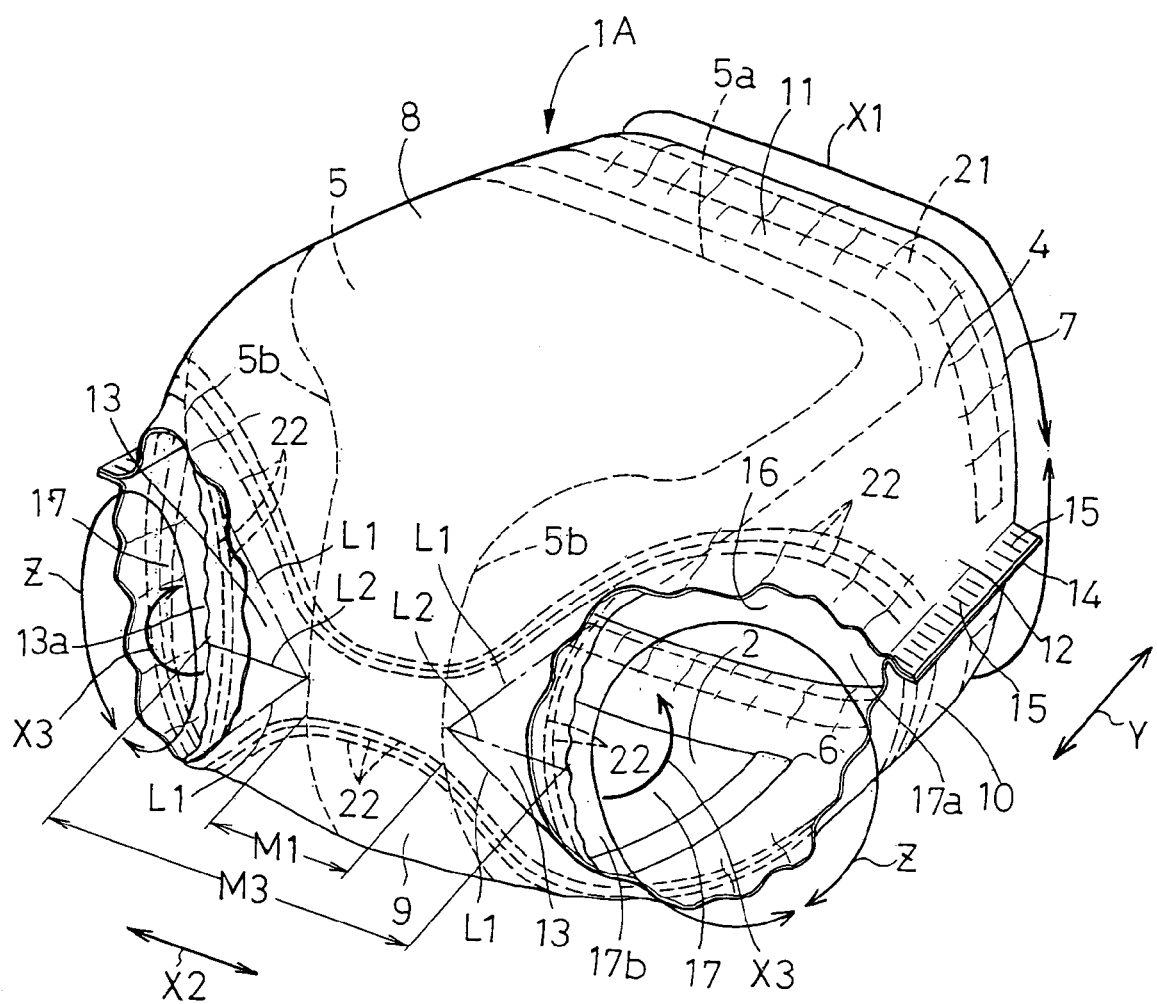
FIG. 2 is a perspective view showing this article prior to tucking the leg-surrounding flaps into the respective leg-holes.
Figure 3:
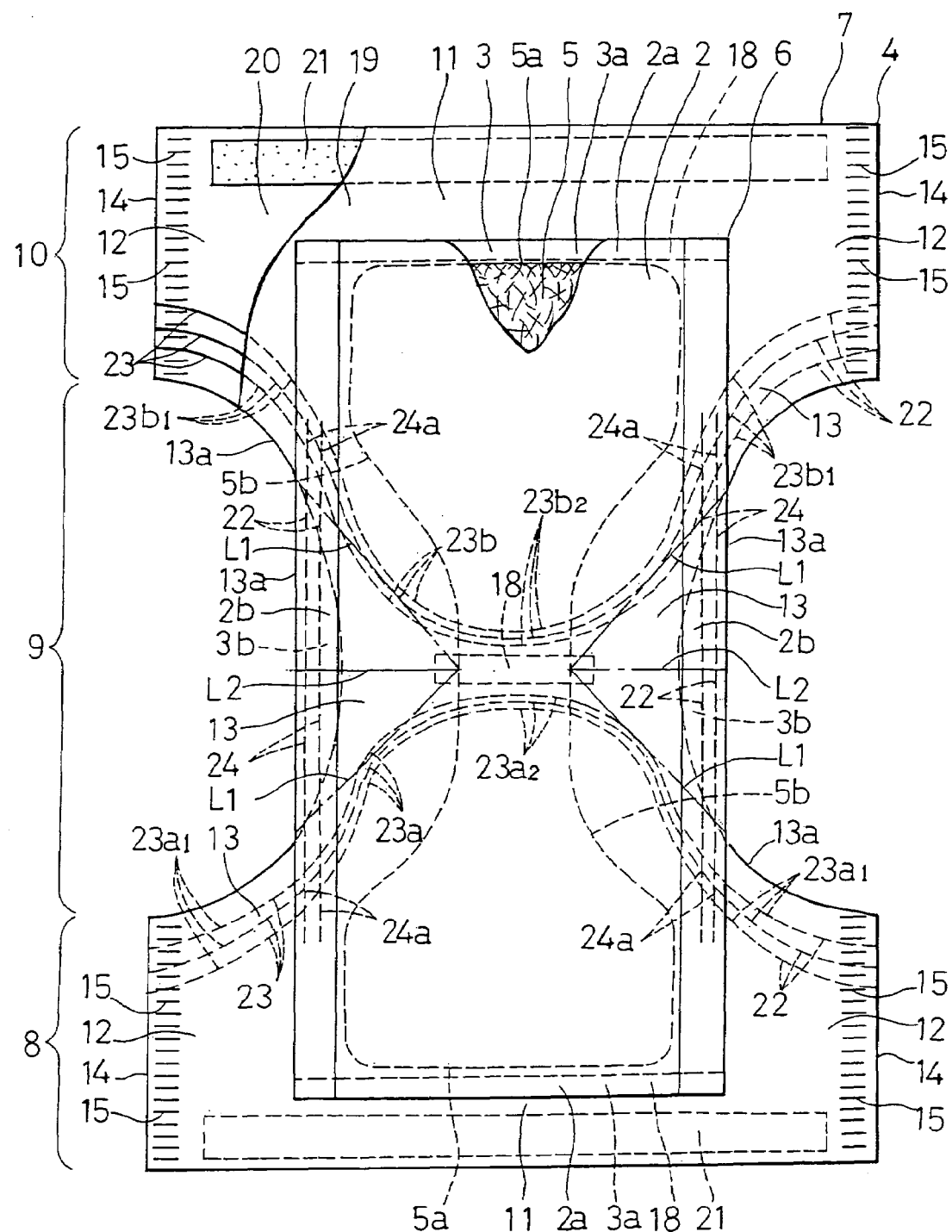
FIG. 3 is a partially cutaway developed plan view showing the article of FIG. 2 with the front and rear waist regions disconnected from each other.
Figure 4:
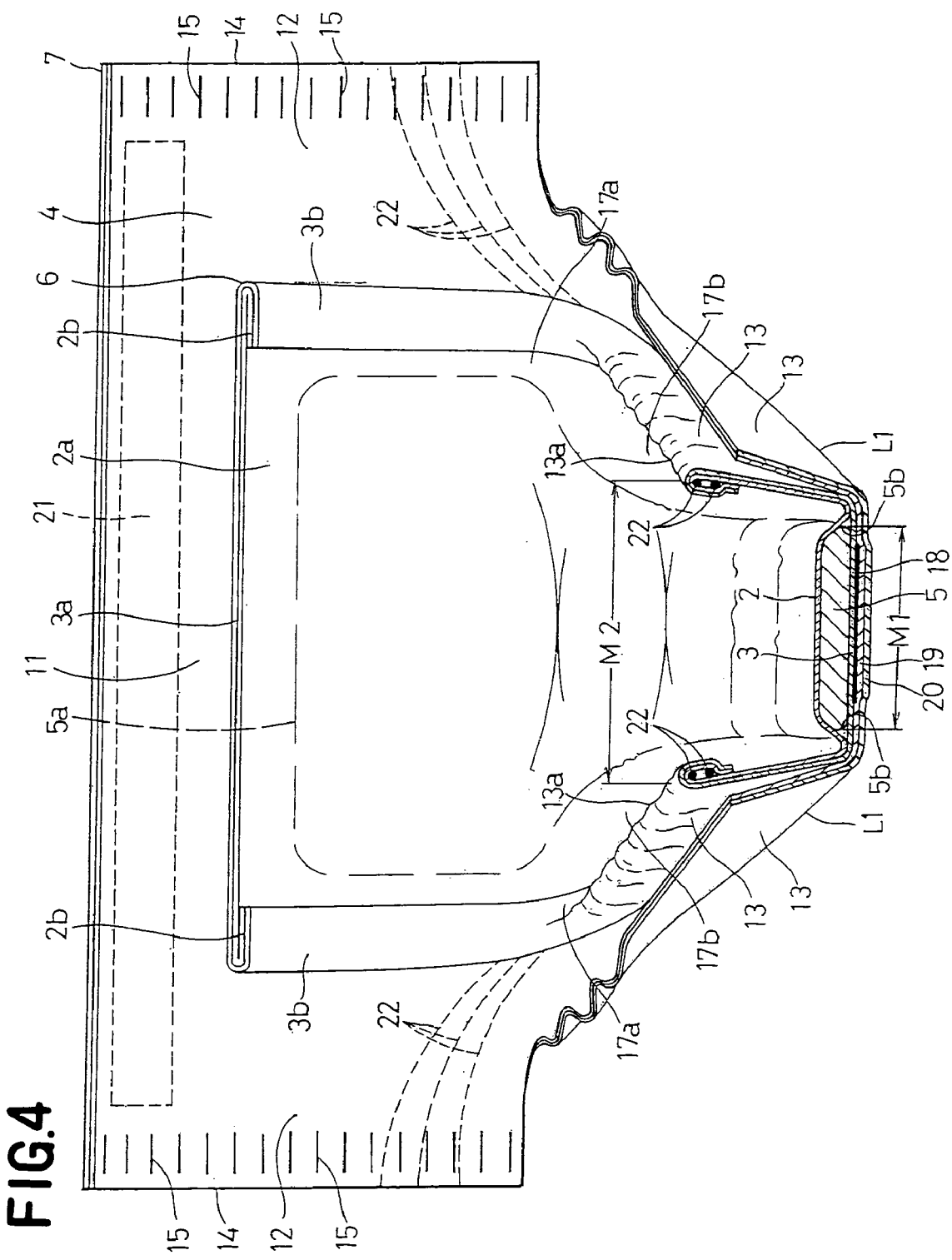
FIG. 4 is a sectional view taken along a line A—A in FIG.1.

FIG. 1 is a perspective view showing a disposable wearing article 1A, FIG. 2 is a perspective view showing the article 1A as before leg-surrounding flaps 13 are tucked inward of respective leg-holes 17, FIG. 3 is a partially cutaway developed plan view showing the article 1A of FIG. 1 with front and rear waist regions 8, 10 disconnected from each other, and FIG. 4 is a sectional view taken along a line A—A in FIG. 1. Referring to FIGS. 1 and 2, a waist-surrounding direction is indicated by an arrow X1, a transverse direction is indicated by an arrow X2, a longitudinal direction is indicated by an arrow Y and a leg-surrounding direction is indicated by an arrow Z. Expression "inner surfaces of a topsheet 2, a backsheet 3 and an outer sheet 4, respectively" should be understood to be the surfaces of these sheets facing a first panel 5 and expression "outer surfaces of these sheets 2, 3, 4" should be understood to be the surfaces of these sheets facing away from the first panel 5.

The article 1A comprises the rectangular liquid-pervious topsheet 2 (liquid-pervious sheet) facing a wearer's body, the rectangular liquid-impervious backsheet 3 (liquid-impervious sheet) facing away from the wearer's body, a liquid-impervious outer sheet 4 (liquid-impervious sheet) lying outside the backsheet 3 and having an area larger than both the top- and backsheets 2, 3, and a liquid-absorbent first panel 5 interposed between the top- and backsheets 2, 3 and firmly attached to the inner surface of at least one of these sheets 2, 3. In the article 1A, the top- and backsheets 2, 3 cooperate with the panel 5 to define a liquid-absorbent pad 6, and the outer sheet 4 defines pants 7.

The article 1A is composed of a front waist region 8, a rear waist region 10 and a crotch region 9 extending between these two waist regions 8, 10. The article 1A has longitudinally opposite end portions 11 extending in the waist-surrounding direction in the front and rear waist regions 8, 10 outside longitudinally opposite ends 5a of the panel 5, respectively, transversely opposite side edge portion 12 extending in the longitudinal direction in the front and rear waist regions 8, 10 outside transversely opposite side edges 5b of the panel 5, and leg-surrounding flaps 13 extending in the leg-surrounding direction in the crotch region 9 outside the transversely opposite side edges 5b of the panel 5.

In the article 1A, the front and rear waist regions 8, 10 are overlaid together in the vicinity of the outermost edges 14 of the transversely opposite side edge portions 12 and firmly bonded together in the vicinity of these outermost edges 14 by a plurality of welding lines 15 arranged intermittently in the longitudinal direction. With the front and rear waist regions 8, 10 of the article 1A connected to each other in this manner, a waist-hole 16 destined to receive the wearer's torso and a pair of leg-holes 17 destined to receive the wearer's legs are defined. In the article 1A, the waist-hole 16 is surrounded by the longitudinally opposite end portions 11 and the leg-holes 17 are surrounded by the respective leg-surrounding flaps 13.

In the front and rear waist regions 8, 10 as well as in a middle zone of the crotch region 9 of the article 1A, the outer surface of the backsheet 3 is firmly bonded to the inner surface of the outer sheet 4 by means of an adhesive 18. Free side edges 13a of the respective leg-surrounding flaps 13 curve inwardly in the transverse direction of the article from tops 17a toward bottoms 17b of the respective leg-holes 17 so that a transverse dimension M3 between the free side edges 13a is minimized in the vicinity of the bottoms 17b of the respective leg-holes 17. The article 1A has a transverse dimension of the crotch region 9 smaller than a transverse dimension of both the front waist region 8 and the rear waist region 10 and presents a substantially hourglass-like planar shape.

The panel 5 extends over the crotch region 9 into the front and rear waist regions 8, 10. In the crotch region 9, the transversely opposite side edges 5b of the panel 5 curve inwardly in the transverse direction of the article 1A. The panel 5 presents an hourglass-like planar shape and has a transverse dimension between the side edges 5b which is minimized in the vicinity of the bottoms 17b of the respective leg-holes 17. In the vicinity of the bottoms 17b of the respective leg-holes 17, the minimum transverse dimension M1 between the side edges 5b of the panel 5 is in a range of 2–9 cm. The minimum transverse dimension M1 less than 2 cm would deteriorate the bodily discharge absorbing capacity of the crotch region 9 in the vicinity of the bottoms 17b of the leg-holes 17. The minimum transverse dimension M1 exceeding 9 cm would lead to inconvenience such that the portion of the panel 5 lying in the vicinity of the bottoms 17b of the leg-holes 17 can not be fitly put in the crotch of the wearer and the panel 5 becomes unacceptably bulky. In consequence, the wearer would experience an uncomfortable feeling during use of the article 1A. Furthermore, the panel 5 would be formed with a plurality of irregular wrinkles as the panel 5 is squeezed in the wearer's crotch.

It should be understood that the planar shape of the panel 5 is not limited to the hourglass-shape but the panel 5 may present a rectangular planar shape so far as the minimum transverse dimension M1 is in the range of 2–9 cm.

The top- and backsheets 2, 3 are overlaid each other along longitudinally outer end portions 2a, 3a outside the longitudinally opposite ends 5a of the panel 5 as well as transversely opposite side edge portions 2b, 3b outside the transversely opposite side edges 5b of the panel 5 and have inner surfaces of these portions 2a, 3a, 2b, 3b firmly bonded to each other, respectively. The top- and backsheets 2, 3 are folded inwardly in the transverse direction of the article 1A along the transversely opposite side edge portions 2b, 3b thereof in the front and rear waist regions 8, 10. The sheets 2, 3 are collapsed inwardly in the transverse direction of the article 1A and in each of the collapsed side edge portions 2b, 3b, the outer surface of the topsheet 2 facing itself is firmly bonded together.

Though not shown, it is possible to provide leak-barrier sheets independently of the top- and backsheets 2, 3 outside the respective side edges 5b of the panel 5. In this case, each of such leak-barrier sheets has a fixed side edge portion fixed to these associated side edge 5b of the panel 5, free side edge portion normally biased to rise above the panel 5 and longitudinally opposite end portions collapsed inwardly in the transverse direction of the article 1A and bonded to the panel 5 outside the associated end portion 5a in such a collapsed state. The free side edge portion is provided with an elastic member extending in the leg-surrounding direction and secured thereto in a stretched state. A stock material for the leak-barrier sheets may be selected from the group consisting of a hydrophobic fibrous nonwoven fabric and a composite sheet comprising a hydrophobic fibrous nonwoven fabric and a liquid-impervious plastic film laminated thereupon.

The longitudinally opposite end portions 11 of the respective waist regions are formed by portions of the outer sheet 4 extending outwardly in the longitudinal direction beyond the longitudinally opposite ends 5a of the panel 5. The transversely opposite side edge portions 12 of the respective waist regions are formed by portions of the outer sheet 4 extending outwardly in the transverse direction beyond the transversely opposite side edges 5b of the panel 5. A stock material for the outer sheet 4 is a composite nonwoven fabric comprising two layers of hydrophobic fibrous nonwoven fabric 19, 20 laminated upon each other. The longitudinally opposite end portions 11 of the respective waist regions are respectively provided with band-like waist-surrounding elastic members 21 extending in the waist-surrounding direction secured thereto in a stretched state. These waist-surrounding elastic members 21 are interposed between the layers of nonwoven fabric 19, 20 and secured to at least one of these layers of nonwoven fabric 19, 20.

The leg-surrounding flaps 13 are formed by portions of the top- and backsheets 2, 3 extending outwardly in the transverse direction beyond the side edges 5b of the panel 5 and portions of the outer sheet 4 extending outwardly in the transverse direction beyond the side edges 5b of the panel 5. The leg-surrounding flaps 13 are provided with a plurality of leg-surrounding elastic members 22 extending in the leg-surrounding direction and secured thereto in a stretched state.

The leg-surrounding flaps 13 are formed with first folding lines L1 and second folding lines L2. The first folding lines L1 extend upwardly in the leg-surrounding direction from the side edges 5b of the panel 5 in the vicinity of the bottoms 17b of the respective leg-holes 17 toward the free side edges 13a of the respective leg-surrounding flaps 13 lying in the vicinity of the tops 17a of the respective leg-holes 17. The second folding lines L2 extend outwardly in the transverse direction from the side edges 5b of the panel 5 lying in the vicinity of the bottoms 17b of the respective leg-holes 17 toward the free side edges 13a of the respective leg-surrounding flaps 13 lying in the vicinity of the bottoms 17b of the respective leg-holes 17. The leg-surrounding flaps 13 are folded along these first and second folding lines L1, L2 and tucked inwardly in the transverse direction of the article 1A into the respective leg-holes 17.

The leg-surrounding elastic members 22 comprise first elastic members 23 secured to the outer sheet 4 and second elastic members 24 secured to the side edge portions 2b, 3b of the top- and backsheets 2, 3, respectively. The first elastic members 23, in turn, comprise elastic members 23a extending from the front waist region 8 toward a transversely middle zone of the crotch region 9 so as to describe circular arcs and elastic members 23b extending from the rear waist region 10 toward the transversely middle zone of the crotch region 9 in the same manner. These elastic members 23a, 23b respectively have opposite lateral sections $23a_1$, $23b_1$ extending over the leg-surrounding flaps 13 in the leg-surrounding direction and middle sections $23a_2$, $23b_2$ extending across the middle zone of the crotch region 9 in the transverse direction. The first elastic members 23 are interposed between the layers of nonwoven fabric 19, 20 and secured to at least one of these nonwoven fabric layers 19, 20.

The second elastic members 24 extend in the leg-surrounding direction between the opposite lateral sections $23a_1$, $23b_1$ of the elastic members 23a, 23b, respectively. These second elastic members 24 are wrapped by the top- and backsheets 2, 3 along the side edge portions 2b, 3b thereof and secured to the outer surface of the topsheet 2.

Of the first and second elastic members 23, 24 constituting the leg-surrounding elastic members 22, the elastic members 23a, 23b constituting the first elastic members 23 intersect longitudinally opposite end sections 24a of the respective second elastic members 24 at the lateral sections $23a_1$, $23b_1$ thereof, respectively so that these elastic members 23, 24 may substantially define continuous curves on the respective leg-surrounding flaps 13.

To erect the article 1A in its state shown in FIG. 1 from its state shown in FIG. 3 in the plan view, the article 1A is folded in the crotch region 9 with the topsheet 2 inside so that the front and rear waist regions 8, 10 may face each other, and then the front and rear waist regions 8, 10 are connected to each other by joining them in the vicinity of the outermost edges 14 of the respective side edge portions 12 of these waist regions 8, 10. Finally, the respective leg-surrounding flaps 13 are folded along the first and second folding lines L1, L2 and these flaps 13 are tucked inwardly in the transverse direction of the article 1A into the respective leg-holes 17 as indicated by the arrow X3 in FIG. 2.

With the leg-surrounding flaps 13 tucked into the respective leg-holes 17 in this manner, the leg-surrounding flaps 13 lying in the vicinity of the bottoms 17b of the respective leg-holes 17 rise above the panel 5 as will be seen in FIG. 4. In the vicinity of the bottoms 17b of the respective leg-holes 17, the free side edges 13a of the leg-surrounding flaps 13 get closer to each other in the transverse direction of the article 1A from the positions thereof in FIG. 2 showing the state before the leg-surrounding flaps 13 are tucked, and thus a transverse spacing dimension between the free side edges 13a of the leg-surrounding flaps 13 is reduced. In the vicinity of the bottoms 17b of the leg-holes 17, now the minimum spacing dimension M2 between the free side edges 13a of the leg-surrounding flaps 13 is substantially same as the minimum transverse dimension M1 between the side edges 5b of the panel 5 and both the minimum spacing dimension M2 and the minimum transverse dimension M1 are in the range of 2–9 cm.

With the leg-surrounding flaps 13 being tucked, the transverse dimension of the crotch region 9 in the vicinity of the bottoms 17b of the respective leg-holes 17 is reduced substantially to the minimum transverse dimension M1 of the panel 5 and thereby the transverse dimension of the crotch region 9 in the vicinity of the bottoms 17b of the respective leg-holes 17 is reduced substantially to the transverse dimension (approximately 3–8 cm) of the wearer's crotch or less. The portion of the crotch 9 lying in the vicinity of the bottoms 17b of the leg-holes 17 is fitly put in the wearer's crotch as the article 1A is put on the wearer's body, so the wearer is free from any uncomfortable feeling. Furthermore, there is no possibility that the leg-surrounding flaps 13 might be irregularly folded and be formed with a plurality of irregular wrinkles even if the crotch region 9 of the article 1A is squeezed in the wearer's crotch. There is no anxiety, therefore, that the bodily discharge absorbing capacity of the crotch region 9 might be deteriorated and any amount of bodily discharges might leak from the crotch region 9.

In the vicinity of the bottoms 17b of the leg-holes 17, the leg-surrounding flaps 13 rising above the panel 5 define barriers against leakage of bodily discharges and serve to prevent any amount of bodily discharges from leaking beyond the bottoms 17b of the leg-holes 17.

Figure 5:
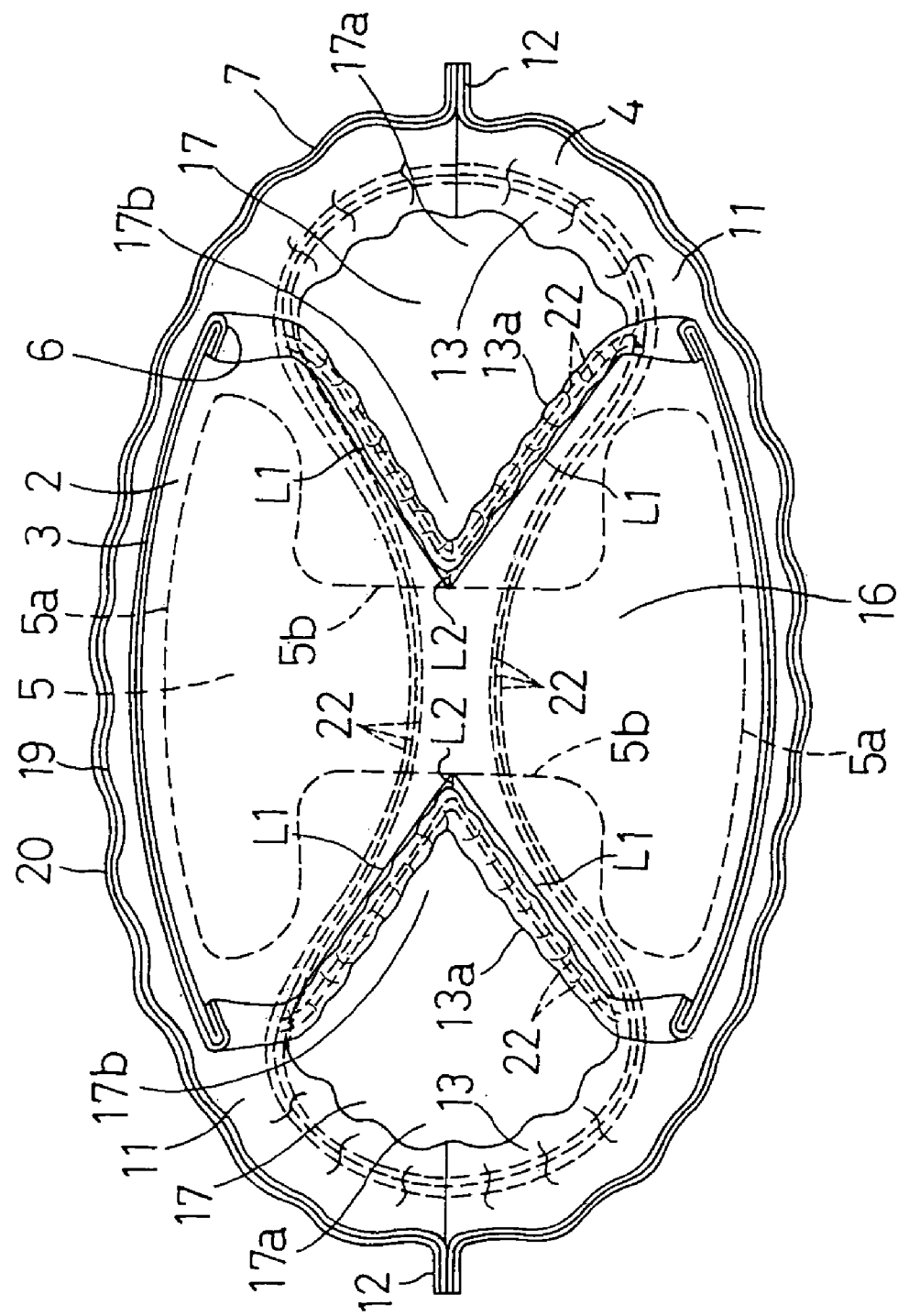
FIG. 5 is a diagram illustrating the article of FIG. 1 with the waist-hole opened, as viewed from above this waist-hole.

FIG. 5 is a diagram illustrating the article 1A of FIG. 1 with the waist-hole 16 opened, as viewed from above this waist-hole 16. By viewing the article 1A from above through the waist-hole 16 being opened, it is found that both the waist-hole 16 and the bottoms 17b of the leg-holes 17 open in the longitudinal direction. It is also found that the bottoms 17b of the leg-holes 17 lie ahead of the waist-hole 16 and are aligned with the leg-holes 17 substantially on straight lines, respectively. Thus, the article 1A is free from inconvenience such that the wearer's toes and/or heels might get stuck with the flaps 13 lying in the vicinity of the bottoms 17b of the leg-holes 17 as the wearer's legs are guided through the waist-hole 16 into the respective leg-holes 17 and consequently there is no anxiety that the operation of wearing the article 1A might be retarded.

Figure 6:
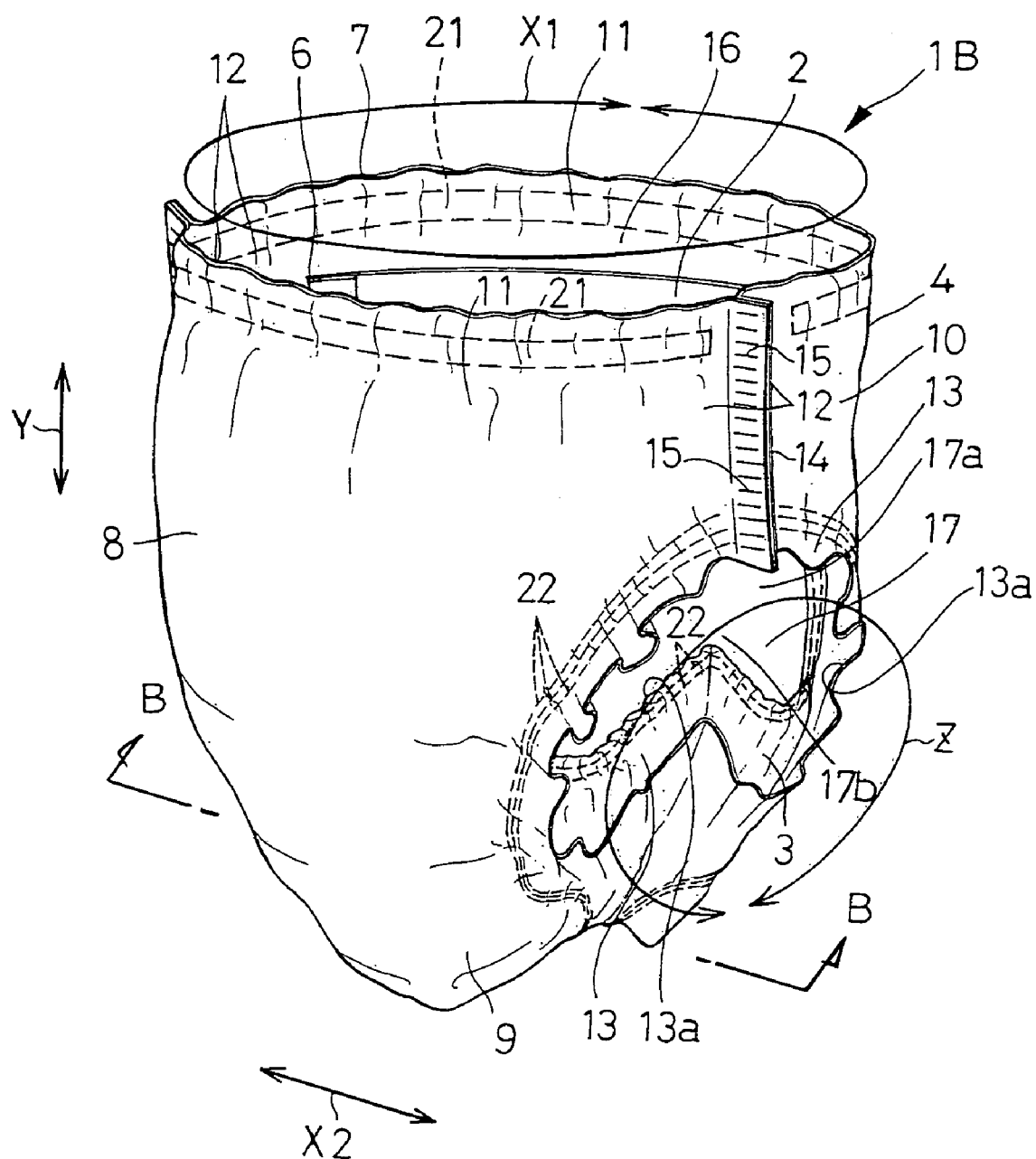
FIG. 6 is a perspective view showing another embodiment of wearing article.
Figure 7:
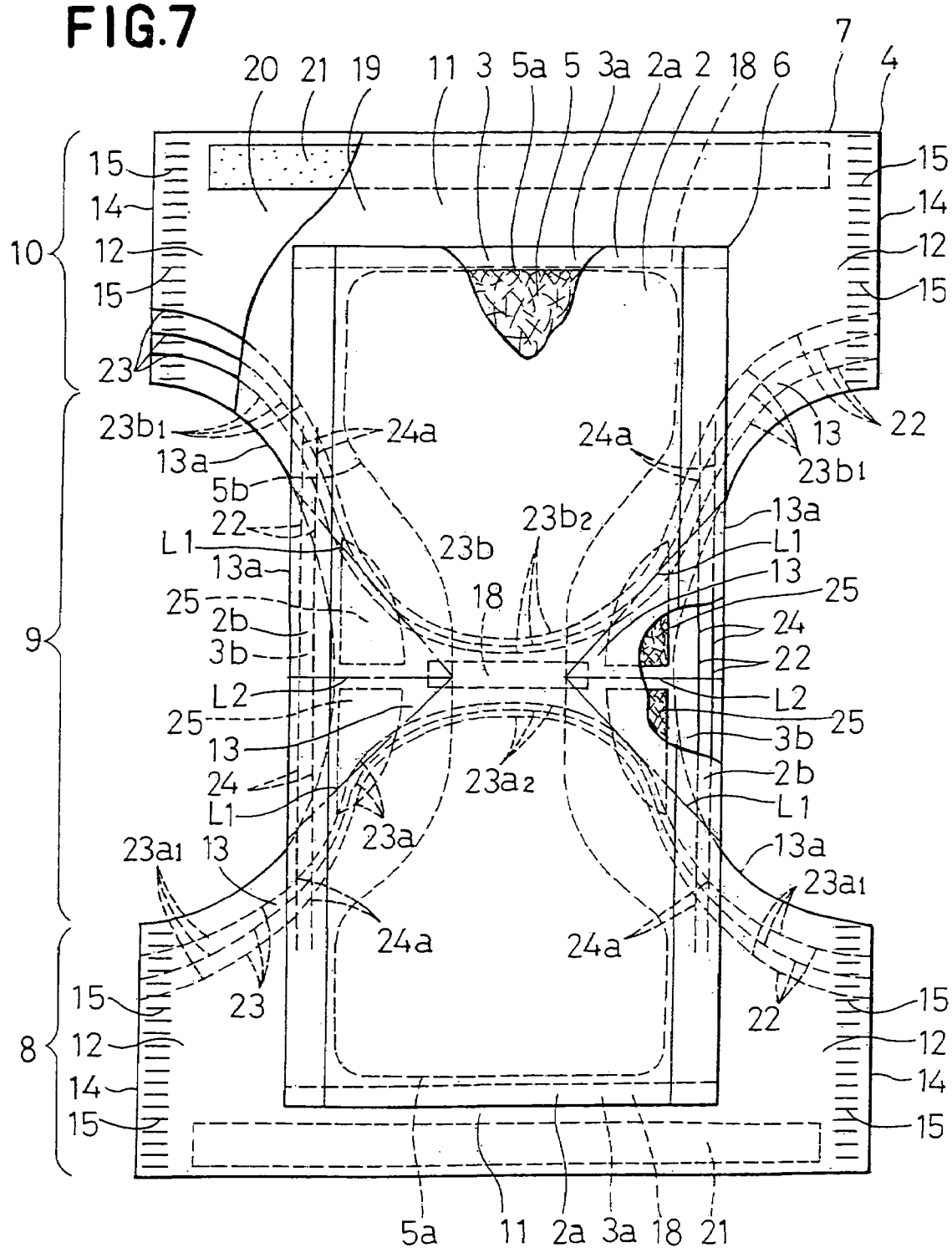
FIG. 7 is a partially cutaway developed plan view showing the article of FIG. 6 with the front and rear waist regions disconnected from each other.
Figure 8:
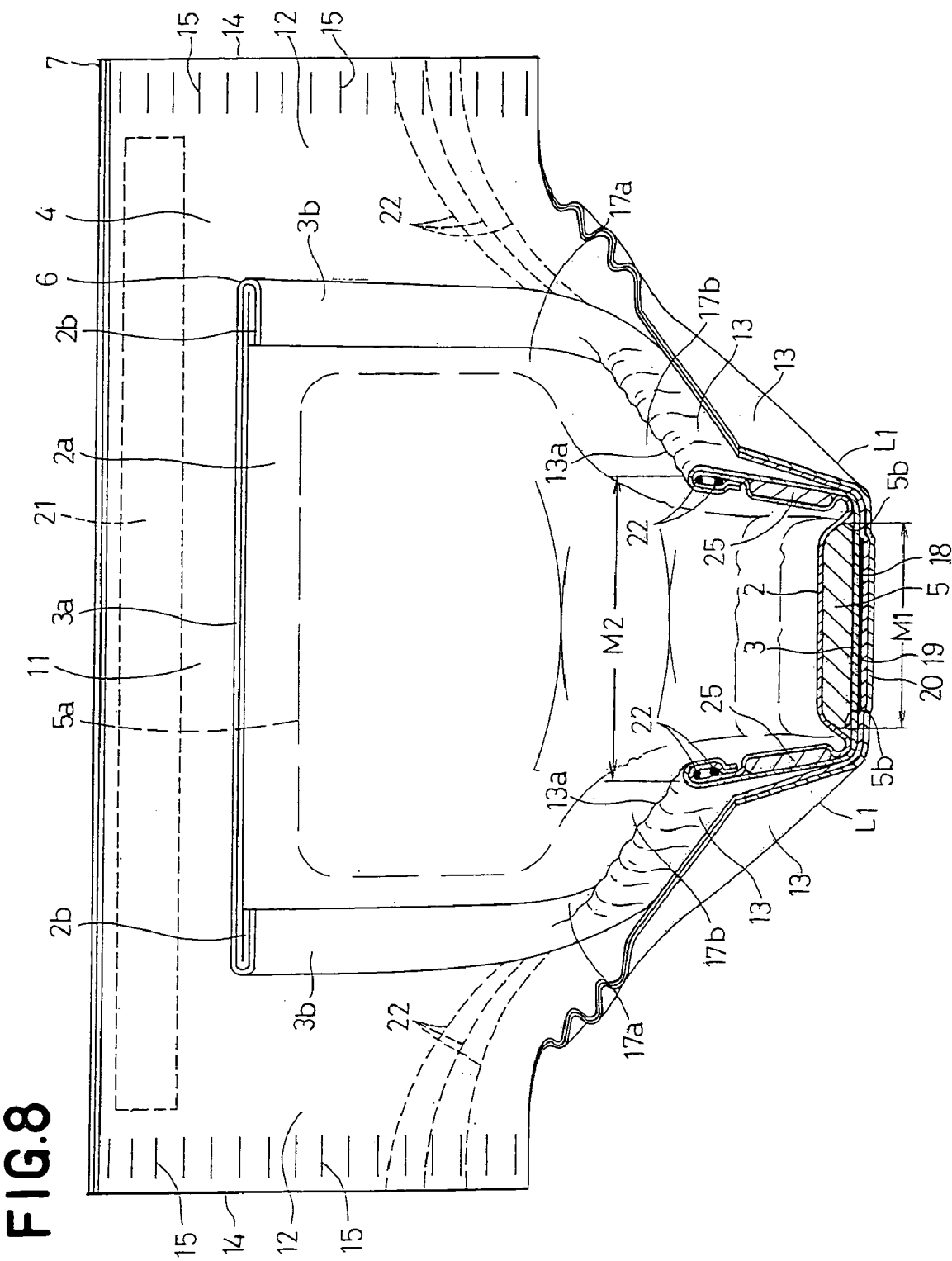
FIG. 8 is a sectional view taken along a line B—B in FIG. 6.
Figure 9:
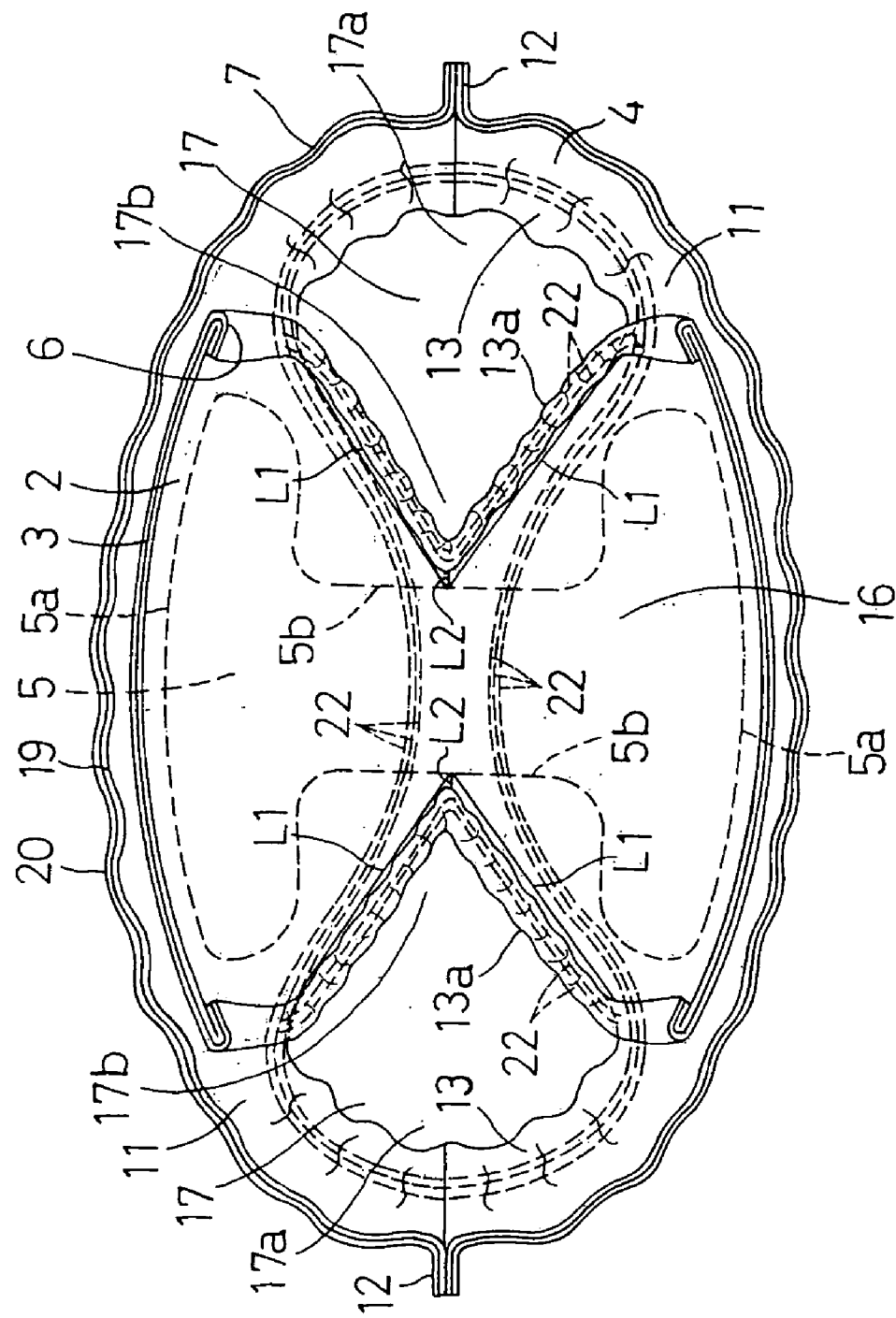
FIG. 9 is a diagram illustrating the article of FIG. 6 with the waist-hole opened, as viewed from above this waist-hole.

FIG. 6 is a perspective view showing another embodiment 1B of a wearing article according to this invention, FIG. 7 is a partially cutaway developed plan view showing the article 1B of FIG. 6 with the front and rear waist regions 8, 10 disconnected from each other, FIG. 8 is a sectional view taken along a line B—B in FIG. 6 and FIG. 9 is a diagram illustrating the article 1B of FIG. 6 with the waist-hole 16 opened, as viewed from above this waist-hole 16. Referring to FIG. 6, the waist-surrounding direction is indicated by the arrow X1, the transverse direction is indicated by the arrow X2, the longitudinal direction is indicated by the arrow Y and the leg-surrounding direction is indicated by the arrow Z.

The article 1B also comprises the liquid-pervious topsheet 2 (liquid-pervious sheet) facing the wearer's body, the liquid-impervious backsheet 3 (liquid-impervious sheet) facing away from the wearer's body, a liquid-impervious outer sheet 4 (liquid-impervious sheet) lying outside the backsheet 3, and a liquid-absorbent first panel interposed between the top- and backsheets 2, 3, and the leg-surrounding flaps 13 are formed with the first and second folding lines L1, L2. However, the article 1B is distinguished from the article 1A of FIG. 1 in the aspect as will be described below.

In the article 1B, the liquid-absorbent second panels 25 are placed between the vicinities of the respective first folding lines L1 and the free side edges 13a of the respective leg-surrounding flaps 13 as shown in FIG. 7. The second panels 25 are interposed between the top- and backsheets 2, 3 and secured to the inner surface of at least one of these sheets 2, 3. On the second folding lines L2 as well as in the vicinity of these second folding lines L2, none of the second panels 25 is present.

In this article 1B, the top- and backsheets 2, 3 cooperate with the first and second panels 5, 25 to define a liquid-absorbent pad 6, and the outer sheet 4 defines pants 7. The first panel 5 has an hourglass-like planar shape and a transverse dimension between its transversely opposite side edges 5b is minimized in the vicinity of the bottoms 17b of the respective leg-holes 17. Similarly to the case shown in FIG. 1, this minimum transverse dimension M2 between the transversely opposite side edges 5b of the first panel 5 in the vicinity of the bottoms 17b of the respective leg-holes 17 is in a range of 2–9 cm.

The first folding lines L1 extend in the leg-surrounding direction from the side edges 5b of the first panel 5 in the vicinity of the bottoms 17b of the respective leg-holes 17 toward the free side edges 13a of the respective leg-surrounding flaps 13 lying in the vicinity of the tops 17a of the respective leg-holes 17. The second folding lines L2 extend outwardly in the transverse direction from the side edges 5b of the panel 5 lying in the vicinity of the bottoms 17b of the respective leg-holes 17 toward the free side edges 13a of the respective leg-surrounding flaps 13 lying in the vicinity of the bottoms 17b of the respective leg-holes 17. In the case of the article 1B, the leg-surrounding flaps 13 are folded along these first and second folding lines L1, L2 and tucked together with the second panels 25 inwardly in the transverse direction of the article 1B into the respective leg-holes 17.

To erect the article 1B in its state shown in FIG. 6 from its state shown in FIG. 7 in the plan view, the article 1B is folded in the crotch region 9 with the topsheet 2 inside so that the front and rear waist regions 8, 10 may face each other, and then the front and rear waist regions 8, 10 are connected to each other by joining them in the vicinity of the outermost edges 14 of the respective side edge portions 12 of these waist regions 8, 10. Finally, the respective leg-surrounding flaps 13 are folded along the first and second folding lines L1, L2 and these flaps 13 are tucked inwardly in the transverse direction of the article 1B into the respective leg-holes 17.

In the case of the article 1B also, the leg-surrounding flaps 13 lying in the vicinity of the bottoms 17b of the respective leg-holes 17 rise together with the second panels 25 above the first panel 5 as will be seen in FIG. 8 as the leg-surrounding flaps 13 are tucked into the respective leg-holes 17 along the first and second folding lines L1, L2. In the vicinity of the bottoms 17b of the respective leg-holes 17, the free side edges 13a of the leg-surrounding flaps 13 get closer to each other in the transverse direction of the article 1B and thus a transverse spacing dimension between the free side edges 13a of the leg-surrounding flaps 13 is reduced. In the vicinity of the bottoms 17b of the leg-holes 17, the minimum spacing dimension M2 between the free side edges 13a of the leg-surrounding flaps 13 is substantially same as the minimum transverse dimension M1 between the side edges 5b of the first panel 5.

With the leg-surrounding flaps 13 being tucked, the transverse dimension of the crotch region 9 in the vicinity of the bottoms 17b of the respective leg-holes 17 is reduced substantially to the minimum transverse dimension M1 of the panel 5 and thereby the transverse dimension of the crotch region 9 in the vicinity of the bottoms 17b of the respective leg-holes 17 is reduced substantially to the transverse dimension of the wearer's crotch or less. The portion of the crotch region 9 lying in the vicinity of the bottoms 17b of the leg-holes 17 is fitly put in the wearer's crotch as the article 1B is put on the wearer's body, so the wearer is free from any uncomfortable feeling. Furthermore, there is no possibility that the leg-surrounding flaps 13 might be irregularly folded and/or the first panel 5 might be formed with a plurality of irregular wrinkles even if the crotch region 9 of the article 1B is squeezed in the wearer's crotch. There is no anxiety, therefore, that the bodily discharge absorbing capacity of the crotch region 9 might be deteriorated and any amount of bodily discharges might leak from the crotch region 9.

In the vicinity of the bottoms 17b of the leg-holes 17, the leg-surrounding flaps 13 and the second panels 25 rising above the first panel 5 define barriers against leakage of bodily discharges and serve to prevent any amount of bodily discharges from leaking beyond the bottoms 17b of the leg-holes 17. In the vicinity of the bottoms 17b of the respective leg-holes 17, not only the first panel 5 but also the second panels 25 function to absorb bodily discharges and thereby the article 1B is capable to absorb much more amount of bodily discharges than the article 1A of FIG. 1 in the vicinity of the bottoms 17b of the respective leg-holes 17.

In the case of the article 1B, the bottoms 17b of the leg-holes 17 lie ahead of the waist-hole 16 and are aligned with the leg-holes 17 substantially on straight lines, respectively, as will be understood from FIG. 9. Thus, the article 1B is free from inconvenience such that the wearer's toes and/or heels might get stuck with the flaps 13 lying in the vicinity of the bottoms 17b of the leg-holes 17 as the wearer's legs are guided through the waist-hole 16 into the respective leg-holes 17 and consequently there is no anxiety that the operation of wearing the article 1A might be retarded. On the second folding lines L2 as well as in the vicinity of these second folding lines L2, none of the second panels 25 is present. Such an arrangement facilitates the leg-surrounding flaps 13 to be folded along the respective second folding lines L2 and, in addition, prevents the leg-surrounding flaps 13 to become bulky after these flaps 13 have been tucked as would occur if the second panels 25 are present on the second folding lines L2 as well as in the vicinity of these second folding lines L2.

In the article 1B, the second panels 25 may be present also on the second folding lines L2 as well as in the vicinity of these second folding lines L2. In this case, the stiffness of the second panels 25 is preferably lower on the second folding lines L2 and in the vicinity of these second folding lines L2 than in the other regions of the second panels 25. In the article 1B, the stiffness of the second panels 25 is preferably lower on the first folding lines L1 as well as in the vicinity of these first folding lines L1 than in the other regions of the second panels 25. In the article 1B, the first panel 5 may be present also on the first folding lines L1 as well as in the vicinity of these first folding lines L1. In this case, stiffness of the first panel 5 is preferably lower on the first folding lines L1 and in the vicinity of these first folding lines L1 than in the other regions of the first panel 5. In order to ensure that the first and second panels 5, 25 have a stiffness lower on the first and second folding lines L1, L2 as well as in the vicinity of these folding lines L1, L2 than in the other regions of these first and second panels 5, 25, for example, a basis weight of at least one of the fluff pulp and the thermoplastic synthetic resin fiber forming these panels may be reduced.

In both the article 1A shown in FIG. 1 and the article 1B shown in FIG. 6, the leg-surrounding flaps 13 can be reliably maintained in respectively tucked states by an arrangement such that the outer surface of the tucked outer sheet 4 lying between the first and second folding lines L1, L2 and the free side edges 13a of the leg-surrounding flaps 13 so as to face itself after the leg-surrounding flaps 13 have been tucked is bonded to itself.

A stock material for the topsheet 2 may be selected from the group consisting of a hydrophilic fibrous nonwoven fabric, a hydrophobic fibrous nonwoven fabric having a plurality of pores and plastic film having a plurality of fine pores. A stock material for the backsheet 3 may be selected from the group consisting of a hydrophobic fibrous nonwoven fabric, a breathable but liquid-impervious plastic film, a composite nonwoven fabric comprising two or more hydrophobic fibrous nonwoven fabric layers laminated one with another and a composite sheet comprising a hydrophobic fibrous nonwoven fabric and a breathable but liquid-impervious plastic film laminated with each other. A stock material for the outer sheet 4 may be selected from the group consisting of a hydrophobic fibrous nonwoven fabric, a breathable but liquid-impervious plastic film and a composite sheet comprising a hydrophobic fibrous nonwoven fabric and a breathable but liquid-impervious plastic film laminated with each other. It is also possible to use, as a stock material for the backsheet 3 and the outer sheet 4, a composite nonwoven fabric comprising a melt blown fibrous nonwoven fabric having a high water-resistance and two layers of spun bond fibrous nonwoven fabric each having a high strength and a high flexibility sandwiching the melt blown fibrous nonwoven fabric.

The type of nonwoven fabric to be used may be selected from the group consisting of spun lace-, needle punch-, melt blown-, thermal bond-, spun bond-, chemical bond- and air-through-types. Component fibers of the nonwoven fabric may be selected from the group consisting of polyolefine-, polyester- and polyamide-based fibers, and core-sheath type or side-by-side type conjugated fibers of polyethylene/polypropylene or polyethylene/polyester.

It is also possible to use, as a stock material for the outer sheet 4, any one of a stretchable hydrophobic fibrous nonwoven fabric, a stretchable liquid-impervious plastic film, a composite nonwoven fabric comprising two or more layers of stretchable composite nonwoven fabric laminated one with another and a composite sheet comprising stretchable hydrophobic fibrous nonwoven fabric and stretchable liquid-impervious plastic film laminated with each other.

It is possible to use melt blown or spun bond nonwoven fabrics as the stretchable nonwoven fabric. It is possible to use, as a component fiber of the stretchable nonwoven fabric, a stretchable fiber obtained by melt spinning thermoplastic elastomer. It is possible to use, as a stock material for the outer sheet 4, a composite nonwoven fabric comprising a stretchable fibrous nonwoven fabric of thermoplastic elastomeric resin fiber and a fibrous nonwoven fabric of crimped fibers obtained by melt spinning thermoplastic synthetic resin selected from the group consisting of polypropylene, polyethylene and polyester and laminated on at least one surface of the stretchable fibrous nonwoven fabric of thermoplastic elastomeric resin.

Each of the first and second panels 5, 25 comprises a mixture of fluff pulp and super-absorbent polymer particles or a mixture of fluff pulp, super-absorbent polymer particles and thermoplastic synthetic resin fibers each compressed to a desired thickness. Preferably, the first and second panels 5, 25 are entirely covered with and bonded to a tissue paper in order to prevent these panels from getting out shapes and/or to retain the polymer particles within the panels 5, 25. The polymer particles may be selected from the group consisting of a starch-based polymer, a cellulose-based polymer and a synthetic polymer.

To join the top- and backsheets 2, 3 to each other, to secure the panels 5, 25 to the top- and backsheets 2, 3 and to secure the elastic members 21, 22 to the leg-surrounding flaps 13, hot melt adhesives or heat-sealing technique such as a heat-sealing or an ultrasonic sealing may be employed.

The pants-type disposable wearing article according to this invention has the advantageous effects that the leg-surrounding flaps lying in the vicinity of the bottoms of the respective leg-holes rise above the first panel and, at the same time, the free side edges of the respective leg-surrounding flaps get nearer to each other in the vicinity of the bottoms of the respective leg-holes as the leg-surrounding flaps are folded along the first and second folded lines and tucked inwardly in the transverse direction of the article into the respective leg-holes. In consequence, the spacing dimension between the free side edges of the respective leg-surrounding flaps in the vicinity of the bottoms of the respective leg-holes are reduced with respect to this dimension before the leg-surrounding flaps are tucked inwardly. In the article according to this invention, the bottoms of the leg-holes just underlie the waist-hole and are aligned with the leg-holes substantially on straight lines, respectively. Thus, the article is free from inconvenience such that the wearer's toes and/or heels might get stuck with the flaps lying in the vicinity of the bottoms of the leg-holes as the wearer's legs are guided through the waist-hole into the respective leg-holes and consequently there is no anxiety that the operation of wearing the article might be retarded.

With the leg-surrounding flaps being tucked, the transverse dimension of the crotch region in the vicinity of the bottoms of the respective leg-holes is reduced substantially to the transverse dimension of the wearer's crotch or less and the portion of the crotch region lying in the vicinity of the bottoms of the leg-holes is fitly put in the wearer's crotch as the article is put on the wearer's body, so the wearer is free from any uncomfortable feeling. Furthermore, there is no possibility that the leg-surrounding flaps might be irregularly folded or the first panel might be formed with a plurality of irregular wrinkles even if the crotch region of the article is squeezed in the wearer's crotch. There is no anxiety, therefore, that the bodily discharge absorbing capacity of the crotch region might be deteriorated and any amount of bodily discharges might leak from the crotch region. In the vicinity of the bottoms of the leg-holes, the leg-surrounding flaps rising above the panel define barriers against leakage of bodily discharges and serve to prevent any amount of bodily discharges from leaking beyond the bottoms of the leg-holes.

In the article arranged so that the minimum spacing dimension between the free side edges of the respective leg-surrounding flaps substantially corresponds to the minimum transverse dimension between the opposite side edges of the first panel in the vicinity of the bottoms of the respective leg-holes, the minimum width of the first panel may be dimensioned so as to be fitly received in the wearer's crotch to fit the portion of the crotch region in the wearer's crotch.

In the article arranged so that the second panels are respectively provided between the first folding lines and the free side edges of the leg-surrounding flaps, these second panels also serve to absorb bodily discharges and enable the article to absorb much more amount of bodily discharges in the vicinity of the bottoms of the leg-holes. In such article, the second panels rise above the first panel together with the leg-surrounding flaps lying in the vicinity of the bottoms of the leg-holes as the leg-surrounding flaps and the second panels are tucked inwardly along the first and second folding lines in the transverse direction of the article into the respective leg-holes. In this article, the leg-surrounding flaps and the second panels rising above the first panel in the vicinity of the bottoms of the leg-holes form the barriers against leakage of bodily discharges and prevent any amount of bodily discharges from leaking beyond the bottoms of the respective leg-holes.

In the article arranged so that the second panels have relatively low stiffness or none of these second panels is present on the second folding lines as well as in the vicinity of these second folding lines, the leg-surrounding flaps can be more easily folded along the respective second folding lines and, in addition, the leg-surrounding flaps can be prevented from becoming bulky after these flaps have been tucked as would occur if the second panels are present on the second folding lines as well as in the vicinity of these second folding lines.

What is claimed is:

1. A pants-type disposable wearing article, comprising:
   a liquid-pervious sheet, a liquid-impervious sheet, and a liquid-absorbent panel between said sheets;
   a waist-hole and a pair of leg-holes surrounded by leg-surrounding flaps extending in a leg-surrounding direction outside transversely opposite side edges of said panel, wherein a transverse dimension between said transversely opposite side edges of said panel is minimized at bottoms of the leg-holes;
   first folding lines extending from the respective side edges of said panel at said bottoms of said leg-holes toward side edges of the respective leg-surrounding flaps lying at tops of said leg-holes;
   second folding lines extending outwardly in a transverse direction from the respective side edges of said panel lying at said bottoms of said leg-holes toward said side edges of the respective leg-surrounding flaps lying at said bottoms of said leg-holes; and
   leg-surrounding elastic members extending in said leg-surrounding direction and being secured in a stretched state to said leg-surrounding flaps;
   wherein
   said leg-surrounding flaps lying at said bottoms of said leg-holes rise on said panel and said side edges of said leg-surrounding flaps get nearer to each other in said transverse direction with said leg-surrounding flaps being folded along said first and second folding lines and tucked inwardly in said transverse direction into a tucked state; a minimum spacing between said side edges of said leg-surrounding flaps is substantially same as a minimum transverse dimension between said side edges of said panel at said bottoms of said leg-holes;
   said leg-surrounding flaps are free of absorbent material; and each of said leg-surrounding elastic members comprises a plurality of elastic strands running along side each other and getting closer to each other as said strands extend toward the crotch region.

2. The wearing article according to claim 1, wherein the minimum transverse dimension between said side edges of said panel is in a range of 2–9 cm at said bottoms of said leg-holes.

3. The wearing article according to claim 1, wherein said side edges of said leg-surrounding flaps are curved in said transverse direction inwardly of said article from said tops toward said bottoms of said leg-holes so that the minimum spacing between said side edges of said leg-surrounding flaps is at said bottoms of said leg-holes.

4. The wearing article according to claim 1, wherein absorbent material of said liquid-absorbent panel is not folded along said first and second folding lines.

5. A pants-type disposable wearing article having longitudinal and transverse directions, said article comprising:
   a liquid impervious cover sheet defining front and rear regions and a crotch region extending in the longitudinal direction between said front and rear regions;
   a pad comprising a liquid-pervious topsheet, a liquid-impervious backsheet attached to an upper side of said cover sheet, and a liquid-absorbent core interposed between said topsheet and
   wherein
   transversely opposite side edges of said cover sheet in the crotch region are inwardly curved;
   the transversely opposite side edges of said cover sheet in the front and rear regions are attached to each other to define a waist hole and a pair of leg holes;
   said core has a hourglass shape having a minimal transverse dimension in said transverse direction in a longitudinally middle zone of said crotch region;
   at least one of said topsheet and backsheet extends laterally outwardly beyond transversely opposite side edges of said core to define transversely opposite side edges of said pad;
   the transversely opposite side edges of said pad intersect the inwardly curved, transversely opposite side edges of said cover sheet and define, together with said inwardly curved, transversely opposite side edges of said cover sheet, peripheral edges of said leg holes;
   transversely opposite lateral portions of said at least one of said topsheet and backsheet in the crotch region are folded along a pair of folding lines and tucked inwardly of the article;
   each of said folding lines includes two sections defining a V shape and extending from one of transversely opposite side edges of said core in the middle zone of said crotch region upwardly towards the front and rear regions, respectively, and up to the peripheral edges of said leg holes;
   the transversely opposite lateral and inwardly tucked portions of said at least one of said topsheet and backsheet are free of absorbent material; and
   said core is not folded along said folding lines;
   said article further comprising leg-surrounding elastic members extending along the peripheral edges of said leg holes and being secured in a stretched state to said cover sheet;
   wherein each of said leg-surrounding elastic members comprises a plurality of elastic strands running along side each other and getting closer to each other as said strands extend toward the crotch region.

* * * * *